(12) United States Patent
Kato

(10) Patent No.: US 6,595,914 B2
(45) Date of Patent: Jul. 22, 2003

(54) ELECTRIC BENDING ENDOSCOPE DEVICE OPERATING DURING POWER FAILURES

(75) Inventor: Shingo Kato, Sagamihara (JP)

(73) Assignee: Olympus Optical Co., Ltd., Tokyo (JP)

( * ) Notice: Subject to any disclaimer, the term of this patent is extended or adjusted under 35 U.S.C. 154(b) by 119 days.

(21) Appl. No.: 09/819,960

(22) Filed: Mar. 28, 2001

(65) Prior Publication Data

US 2001/0027268 A1 Oct. 4, 2001

(30) Foreign Application Priority Data

Mar. 31, 2000 (JP) ........................................ 2000-099326

(51) Int. Cl.[7] .............................................. A61D 1/008
(52) U.S. Cl. ........................ 600/152; 600/146; 600/150; 600/151
(58) Field of Search ........................... 600/146, 150–152

(56) References Cited

U.S. PATENT DOCUMENTS 4,924,852 A * 5/1990 Suzuki et al. ............... 600/150
5,373,317 A 12/1994 Salvati et al.
5,624,380 A * 4/1997 Takayama et al. .......... 600/141

FOREIGN PATENT DOCUMENTS

JP 5-46594 * 3/1993 ............ A61B/1/00

* cited by examiner

*Primary Examiner*—John Mulcahy
(74) *Attorney, Agent, or Firm*—Scully, Scott, Murphy & Presser

(57) ABSTRACT

The electric bending endoscope device according to the present invention comprises: an endoscope having a bending portion; a bending control mechanism for electrically driving the bending portion of the endoscope; a power source voltage monitoring portion for monitoring the source voltage supplied to this bending control mechanism; and a change-over switch for releasing the bent state of the bending portion, when the above-mentioned bending portion is in a bent state, on the basis of an output signal from the source voltage monitoring portion.

6 Claims, 3 Drawing Sheets

ELECTRIC BENDING ENDOSCOPE DEVICE OPERATING DURING POWER FAILURES

This application claims benefit of Japanese Application No. 2000-99326 filed in Japan on Mar. 31, 2000, the content of which is incorporated in this reference.

BACKGROUND OF THE INVENTION

1. Field of the Invention

The present invention relates to an electric bending endoscope device, which is provided with an endoscope wherein a bending portion is bent by electrical driving means.

2. Description of the Related Art

Conventionally, a long, thin endoscope is inserted into jet engines or pipes in power plants and observations and various procedures are performed. Typically, a soft insert portion, formed in the endoscope, is provided with a bending portion. This endoscope is provided with a bending apparatus f or bending the bending portion by moving a pulling element such as a bending wire which is passed through the bending portion.

By using this bending apparatus, insertion into a subject area, for example, can be performed easily, while the optical monitoring system disposed on the end of the endoscope insert portion is oriented towards the object.

Recent endoscopes use electric motors to power the bending apparatus. In effect, the bending portion is bent by moving the bending wire with the driving power of the electric motor. By bending the bending portion with an electric motor, the bending operation is significantly improved compared to conventional manual systems. The electric motor of the bending apparatus is powered by an external power source such as a battery or an AC power source.

However, for a bending apparatus using a power source such as the above-mentioned battery, the bending portion will become fixed in the bent position if the battery fails or if the battery voltage drops when the bending portion is being bent. On the other hand, for a bending apparatus using an AC power source as the power source, the operation of the entire apparatus will halt and the bending portion will become fixed in the bent position in the event of a power failure.

For this reason, in order to withdraw the insert portion when there are problems with the power supply, it is necessary to wait until the power is recovered, and then to release the bent state and withdraw the device, when the power source is an AC power source. On the other hand, when the power source is a battery or the like, it is necessary to recharge the battery or replace the battery, and then release the bent state and withdraw the device.

On the other hand, when withdrawing the insert portion from the pipe or the like while the bent state is maintained, a corresponding amount of time is required to withdraw the insert portion because the bending portion is in a bent state. Even when the bent insert portion is withdrawn, for example, the tip of the insert portion that is in the bent state becomes problematic, when storing this insert portion in a storage case, and it becomes impossible to store the device properly.

SUMMARY OF THE INVENTION

It is an object of the present invention to provide an electric bending endoscope device that will facilitate the withdrawal of the insert portion, even when the bending operation of the bending portion cannot be performed because of a problem with the power source, such as a battery failure or power failure, when the bending portion is in the bent state.

Basically, the electric bending endoscope device according to the present invention comprises: an endoscope having a bending portion; a bending control mechanism which electrically drives the bending portion of the endoscope; a source voltage monitoring portion for monitoring the source voltage supplied to this bending control mechanism; and a change-over switch for releasing the bent state of this bending portion, when the above-mentioned bending portion is in the bent state, based on the output signal from this source voltage monitoring portion; wherein it is possible to release the bent state of the bending portion and withdraw the insert portion, even when it becomes impossible to perform the bending operation due to a battery failure or the like, while the bending portion is in the bent state.

DESCRIPTION OF THE PREFERRED EMBODIMENTS

The preferred embodiments of the present invention are explained below with reference to the drawings.

Figure 1:
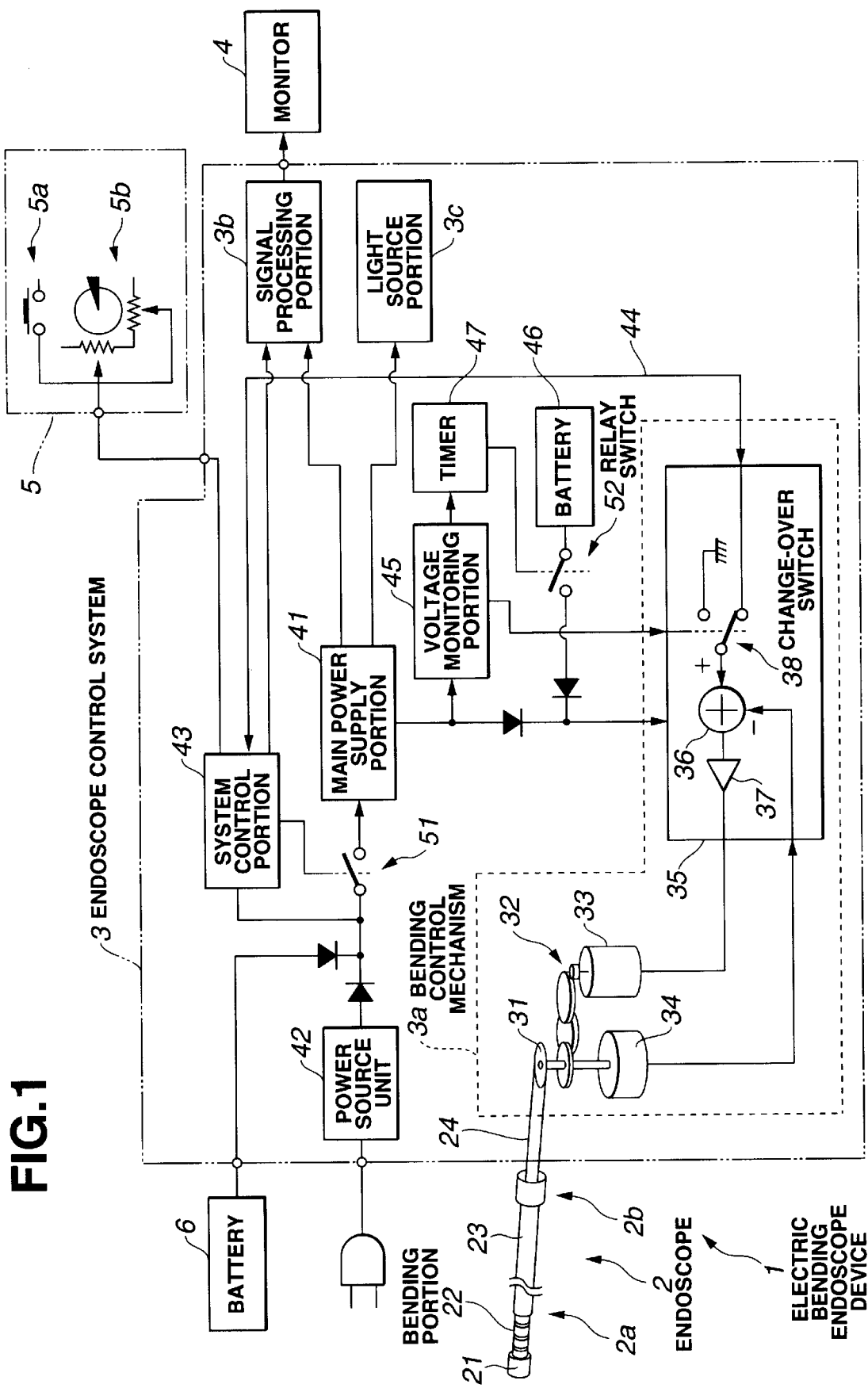
FIG. 1 is a drawing to explain the constitution of the endoscope device according to an embodiment of the present invention.

The electric bending endoscope device 1 according to the present invention is explained with reference to FIG. 1. In the following explanation, a vertical bending wire 24 for upwards and downwards bending is explained. For reasons of simplicity, the constitution relating to a horizontal bending wire having the same constitution as this vertical bending wire 24 is not shown and an explanation is omitted.

As shown in the drawing, the electric bending endoscope device 1 according to the present embodiment is constituted mainly with: an endoscope 2 with an electric bending system, wherein the bending portion 22 constituting the endoscope insert portion 2a is electrically bent; an endoscope control device 3 for electrically driving the bending of the bending portion 22 of the endoscope 2 by a prescribed amount; a monitor 4 that is a display device for displaying the endoscope image; and a remote control device 5, wherein are established a power switch 5a, for turning the power source of the above-mentioned endoscope control device 3 ON and OFF, and a bending angle command portion, such as a joystick 5b, for commanding the bending angle of the above-mentioned bending portion 22.

The above-mentioned endoscope 2 is provided with a long and thin insert portion 2a that is inserted as far as the subject area and an operating portion 2b that doubles as a grasping portion.

The above-mentioned insert portion 2a comprises the following connected in order from the end thereof: a hard end portion 21; a bending portion 22 formed to bend freely vertically and horizontally, for example, and wherein a plurality of bending barrels, not shown, is connected serially to this hard end portion 21; and a flexible tube portion 23 which is long and thin and is connected with this bending portion 22.

An optical monitoring system having an imaging element such as a CCD, for example, and an illuminating optical system for emitting illuminating beams towards the subject area are housed within the above-mentioned hard end portion 21.

A horizontal bending wire, not shown, and a vertical bending wire 24 for bending the above-mentioned bending portion 22, extend from the above-mentioned operating portion 2b into the above-mentioned endoscope control device 3.

Components located within the above-mentioned endoscope control device 3 include a bending control mechanism 3a for electrically driving and bending the above-mentioned bending portion 22 by a prescribed amount; a signal processing portion 3b for generating a picture signal from the image signal sent through a signal cable, not shown, from the above-mentioned imaging element; and a light source portion 3c for supplying illuminating beams through a bundle of light guide fibers, not shown, to the above-mentioned illuminating optical system.

Moreover, the above-mentioned endoscope control device 3 is powered by a commercial power source or battery 6. Also, the picture signal generated by the above-mentioned signal processing portion 3b is output to the above-mentioned monitor 4.

The bending mechanism of the bending portion 22 is explained hereinbelow.

The middle portion of the above-mentioned vertical bending wire (hereinafter "bending wire") 24 is wrapped around a rotatable vertical pulley (hereinafter "pulley") 31 constituting the bending control mechanism 3a. The above-mentioned bending portion 22 can therefore be bent upwards and downwards by rotating the above-mentioned pulley 31 in the desired direction and moving the above-mentioned bending wire 24.

The above-mentioned bending control mechanism 3a is constituted with: a vertical bending motor (hereinafter "bending motor") 33 comprising a DC motor, for example, which is a drive source for the rotation of the above-mentioned pulley 31; a vertical gear train 32 for transferring the rotary driving power of this bending motor 33 to the pulley 31; a potentiometer 34 for detecting the amount of rotation of the above-mentioned pulley 31; and a motor control portion 35 for applying a prescribed voltage and driving the above-mentioned bending motor 33.

The above-mentioned vertical gear train 32 is constituted to cause a plurality of gears to mesh appropriately and the rotary speed of the above-mentioned bending motor 33 to be reduced, while increasing torque. The rotation of the above-mentioned pulley 31 is thereby optimized by the driving power of the bending motor 33 transmitted through the vertical gear train 32.

A difference computing portion 36, drive amp 37, and change-over switch 38 are established within the above-mentioned motor control portion 35.

The bending angle information that is the operation command signal from the above-mentioned joystick 5b and the value detected by the above-mentioned potentiometer 34 are input to the above-mentioned difference computing portion 36 which performs difference processing.

The above-mentioned drive amp 37 amplifies and outputs the voltage value based on the results of the calculations by the above-mentioned difference computing portion 36.

The above-mentioned change-over switch 38 is the bent state releasing means for outputting the information for fixing the bending angle at 0 degrees, in order to release the bent state, to the difference computing portion 36, when the bending portion 22 is in the bent state, based on the voltage drop detection signal output from the voltage monitoring portion 45 discussed below.

The above-mentioned bending motor 33 performs feedback control so that the bending angle information from the joystick 5b matches the pulley 31 position information, which is the value detected by the potentiometer 34, and causes the bending of the above-mentioned bending portion 22.

Moreover, the same results are obtained with this feedback control circuit, whether constituted entirely with analog integrated circuits or using digital integrated circuits such as a microcomputer or DSP.

A main power supply portion 41 for supplying power to the above-mentioned bending control mechanism 3a, signal processing portion 3b, and light source portion 3c is established within the above-mentioned endoscope control device 3. Power from the above-mentioned commercial source, or battery 6, which is an external source, is supplied through a power supply unit 42, for converting the AC power source to a DC power source, to this main power supply portion 41.

In effect, the commercial power source and battery source have an OR connection by means of a diode to the above-mentioned main power supply portion 41. For this reason, the endoscope control device 3 is driven when either an AC power source or a DC power source, is connected.

Consequently, when an AC power source is connected, the output from the above-mentioned power supply unit 42 is supplied to the system control portion 43 within the endoscope control device 3. When the battery 6 is connected, the output from this battery 6 is supplied to the above-mentioned system control portion 43.

The control signal, indicating ON or OFF, from the above-mentioned power switch 5a established in the above-mentioned remote control device 5 and the control signal, indicating the bending angle of the bending portion 22 from the above-mentioned joystick 5b, are input to the above-mentioned system control portion 43.

When the power switch 5a established in the above-mentioned remote control device 5 is found to be in an ON state by the above-mentioned system control portion 43, the relay switch 51 is switched and the output through the above-mentioned power supply unit 42 or the output from the battery 6 is supplied to the above-mentioned main power supply portion 41. Power is thereby supplied to the bending control mechanism 3a, signal processing portion 3b, and light source portion 3c.

Meanwhile, when the above-mentioned joystick 5b is tilted to command a change in the bending angle of the bending portion 22, a resistance value, corresponding to the angle by which the joystick 5b is tilted, is converted to a voltage and input to the system control portion 43 as an operation command signal.

Bending angle information to cause the bending of the bending portion 22 is then output through the control line 44 from this system control portion 43 to the motor control portion 35 in the above-mentioned bending control mechanism 3a.

Moreover, the bending angle information sent through the above-mentioned control line 44 may be transmitted as either an analog voltage value or a serial or parallel digital value.

When noise occurs while the operation command signal is transmitted from the above-mentioned joystick 5b to the system control portion 43, a noise value is included in the bending angle information output from the system control portion 43 and there is a risk that the above-mentioned bending portion 22 will be bent differently from the operation command from the joystick 5b.

In order to prevent this problem, although a diagram is omitted from the present embodiment, the analog voltage value, obtained from the voltage conversion of the resistance value corresponding to the angle at which the joystick 5b in the remote control device 5 is tilted, undergoes analog/digital conversion. After undergoing serial conversion, the parallel data obtained from the A/D conversion is transmitted to the system control portion 43 by serial communication such as RS232C and a stabilized bending operation is obtained.

A voltage monitoring portion 45, battery 46, and timer 47 are established between the above-mentioned main power supply portion 41 and motor control portion 35.

The above-mentioned voltage monitoring portion 45 determines whether the power supply from the above-mentioned main power supply portion 41 is normal. The above-mentioned battery 46 is taken to be an auxiliary power source for supplying power to the above-mentioned motor control portion 35 instead of the above-mentioned main power supply portion 41. Based on a command signal from the above-mentioned voltage monitoring portion 45, the above-mentioned timer 47 switches the relay switch 52 for a prescribed period of time so that power is supplied from the above-mentioned battery 46 to the above-mentioned motor control portion 35.

Upon detecting that the source voltage output from the main power supply portion 41 has dropped below a prescribed voltage value, the above-mentioned voltage monitoring portion 45 outputs a voltage drop detection signal to report the voltage drop to the motor control portion 35 in the above-mentioned bending control mechanism 3a and the above-mentioned timer 47.

The above-mentioned endoscope control device 3 has an OR connection by means of a diode so that the power supply to the motor control portion 35 in the above-mentioned bending control mechanism 3a is provided from either the main power supply portion 41 or the battery 46.

The above-mentioned battery 46 may be a primary cell such as a manganese cell or alkaline cell, but a secondary cell such as a nickel-cadmium cell or nickel-hydrogen cell will alleviate the task of replacing the battery for the user.

Using an electric double layer capacitor as the secondary cell can reduce the charging time, while making a charging circuit unnecessary when using nickel-cadmium cells or nickel-hydrogen cells and reducing the costs of the device.

When the system control portion 43 detects that the power switch 5a established in the above-mentioned remote control device 5 is in an ON state, the above-mentioned relay switch 51 supplies the output from the power supply unit 42 or the output from the battery 6 to the above-mentioned main power supply portion 41. On the other hand, when it is detected that the above-mentioned power switch 5a is in an OFF state, output to the above-mentioned main power supply portion 41 is stopped.

Status information indicating a motor malfunction or the like output from the above-mentioned bending control mechanism 3a is input to the above-mentioned system control portion 43. For this reason, a warning display or the like, according to the status information input, is displayed on the screen of the above-mentioned monitor 4 through the above-mentioned signal processing portion 3b.

The operation of the endoscope device 1, having the endoscope control device 3 with the constitution as discussed above, is explained next.

The user turns ON the power switch 5a in the remote control device 5 with the endoscope control device 3 connected to a commercial power supply, for example. Thereupon, the relay switch 51 assumes a conducting state and power is supplied to the main power supply portion 41. Power is thereby supplied from the main power supply portion 41 to the above-mentioned bending control mechanism 3a, signal processing portion 3b, and light source portion 3c and the device is then capable of performing endoscopic observation.

Next, the user inserts the insert portion 2a towards the subject area. At this time, the user pushes the insert portion 2a towards the subject area while appropriately operating the joystick 5b and bending the bending portion 22.

When the above-mentioned joystick 5b is operated, the difference between the bending angle information corresponding to the operation of the joystick 5b transmitted from the system control portion 43 and the position information from the potentiometer 34 for detecting the amount of rotation of the pulley 31 that moves the bending wire 24 is calculated with the difference computing portion 36 in the bending control mechanism 3a. Feedback control of the bending motor 33 is performed so that the position information and the above-mentioned bending angle information match and the bending portion 22 is bent in the direction desired by the technician.

When an anomaly in the power supply occurs, due to a drop in source voltage supplied by the battery 6 or a power failure, with the device being used in this state, the voltage monitoring portion 45 detects that the power supply is not passing normally from the main power supply portion 41 to the motor control portion 35, while instantly outputting a voltage drop detection signal to the timer 47 and motor control portion 35.

In the above-mentioned timer 47 that has received this voltage drop detection signal, the relay switch 52 is turned ON and power from the battery 46 is supplied to the bending control mechanism 3a for a prescribed period of time instead of from the above-mentioned main power supply portion 41.

Meanwhile, the change-over switch 38 is operated by the motor control portion 35 which has received this voltage drop detection signal. Thereupon, the bending angle information supplied to the above-mentioned difference computing portion 36 is switched from the bending angle information corresponding to the operation command of the above-mentioned joystick 5b to the information for fixing the bending angle at 0 degrees.

In the above-mentioned motor control portion 35, feedback control of the bending motor 33 is thereby performed so that the bending angle of the bending portion 22 in the bent state becomes 0 degrees and the bent state of the above-mentioned bending portion 22 is released.

Moreover, the period of time set in the above-mentioned timer 47 is time sufficient for driving the above-mentioned bending motor 33 and returning the bending portion 22 from a state of maximum bending to a bending angle of 0 degrees where this bending portion 22 is straight.

Also, the present embodiment is constituted so as to perform an operation to release the bent state, regardless of the bending angle of the above-mentioned bending portion 22, when a power failure occurs or the battery runs out. The present embodiment may also be constituted to be able to deny the detection operation by the voltage monitoring portion 45 or the time count by the timer 47 in the system control portion 43. As a result, the embodiment is caused to perform the operation to release the bending only when the bending command necessary for releasing the bending is output to the motor control portion 35 by the system control portion 43.

Furthermore, the drive amp 37 in the above-mentioned motor control portion 35 may have a direct current output or use pulse width modulation, pulse position modulation, or the like.

In this way, a voltage monitoring portion, for monitoring the source voltage supplied to the motor control portion, and a change-over switch are established in the endoscope control device for electric control of the bending operation of the endoscope bending portion. The change-over switch is for switching and inputting the bending angle information input to the difference computing portion by the above-mentioned motor control portion between the bending angle information corresponding to the operation command from the joystick and the information for fixing the bending angle at 0 degrees for releasing the bent state. As a result, when the voltage monitoring portion detects a problem with the power source such as a drop in the source voltage supplied to the motor control portion due to a power failure, the battery running flat, or a battery failure, the bending angle information input to the difference computing portion is switched from the bending angle information corresponding to the operation command from the joystick to the information for fixing the bending angle at 0 degrees by the voltage drop detection signal output from this voltage monitoring portion. Meanwhile, power from the auxiliary power source can be supplied to the motor control portion and the bent state of the bending portion can be released.

As a result, even in the event of a power failure, battery failure, or when the battery has run flat, the device is prepared for releasing the bent state of the bending portion and withdrawing the insert portion, without replacing the battery, recharging the battery, or waiting for the power to return.

Moreover, when the joystick 5b in the remote control device 5 is operated, the parallel data obtained through A/D conversion undergoes serial conversion and is transmitted by serial communication such as RS232C to the system control portion 43. However, it is also possible to have the above-mentioned parallel data taken up by the CPU and transmitted to the system control portion 43 using software.

Also, because the bending direction of the bending portion 22 maybe either vertical or horizontal, two communications systems, for vertical and horizontal information, may be prepared for sending two items of bending angle information to the system control portion 43. However, by using time division and sending both the vertical and horizontal bending angle information alternately, it is possible to have only one communication system and thus reduce the costs of the communication system.

Figure 2:
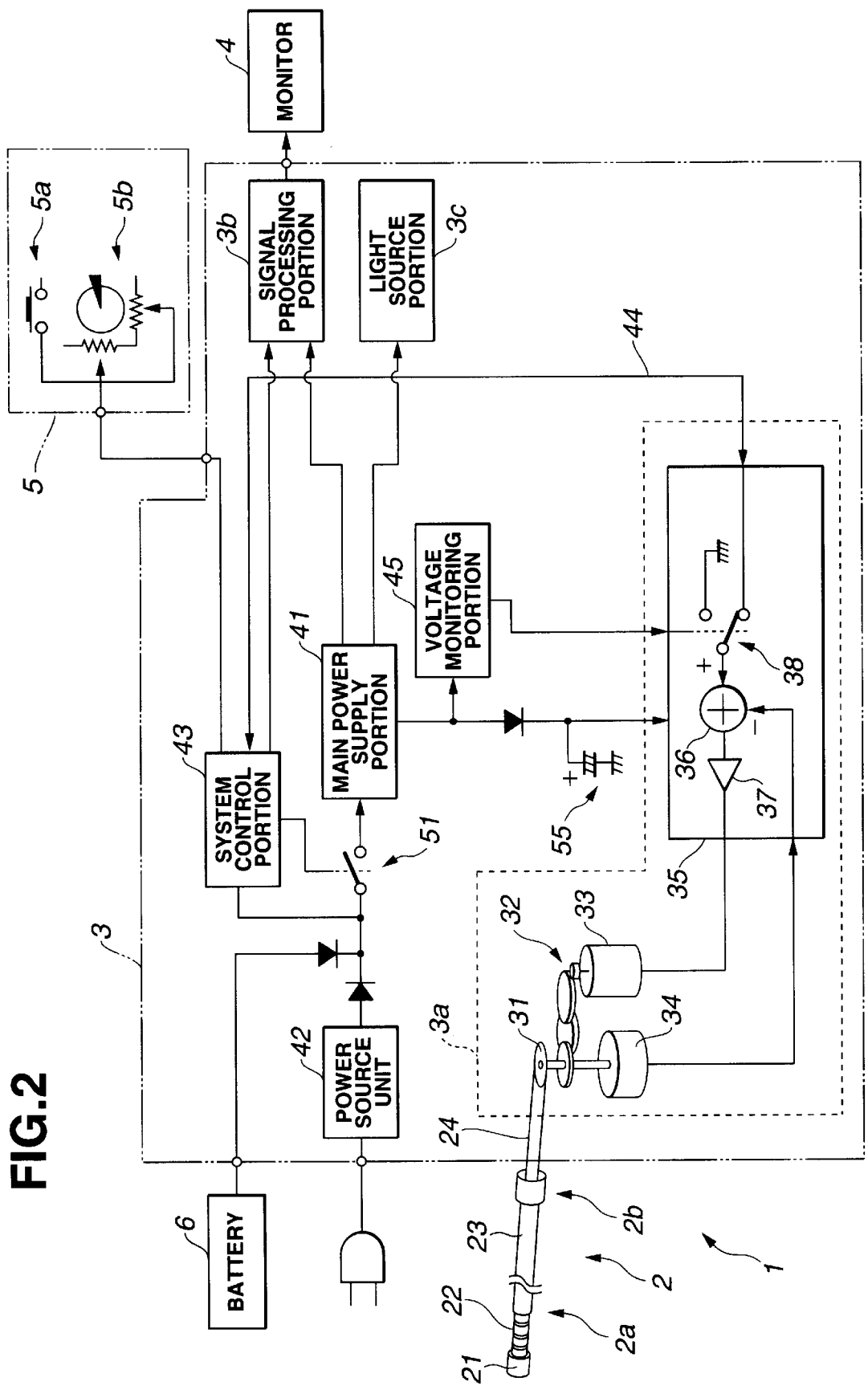
FIG. 2 is a drawing to explain another embodiment of the endoscope control device.

Furthermore, the present embodiment may be constituted so as to release the bending of the bending portion 22, that is in the bent state with the power in the battery 46, when the source voltage supplied from the main power supply portion 41 to the motor control portion 35 drops below a prescribed value. As shown in FIG. 2, it is also possible to establish a smoothing capacitor 55 with a large capacitance on the output side of the main power supply portion 41, instead of the battery 46 and timer 47, and supply the charge stored in this smoothing capacitor 55 to the motor control portion 35 and release the bent state.

In effect, the above-mentioned smoothing capacitor 55 does not contain sufficient power for driving the bending motor 33.

However, when the above-mentioned voltage monitoring portion 45 detects a drop in source voltage and outputs the voltage drop detection signal, the change-over switch 38 of the motor control portion 35 is switched and the information for fixing the bending angle at 0 degrees is supplied to the difference computing portion 36.

The power supplied is insufficient to drive the bending motor 33, with the charge remaining in the above-mentioned smoothing capacitor 55; however, the bending motor 33 is induced to start rotating with this power.

The bending can thereby be released using the way that the tension of the above-mentioned bending wire 24 in the direction for releasing the bending is applied to the bending motor 33 through the pulley 31 and the gear train 32. Other constitutions, operations, and results are the same as with the above-mentioned embodiment; the same numbers are applied to the same elements and an explanation is omitted.

Figure 3:
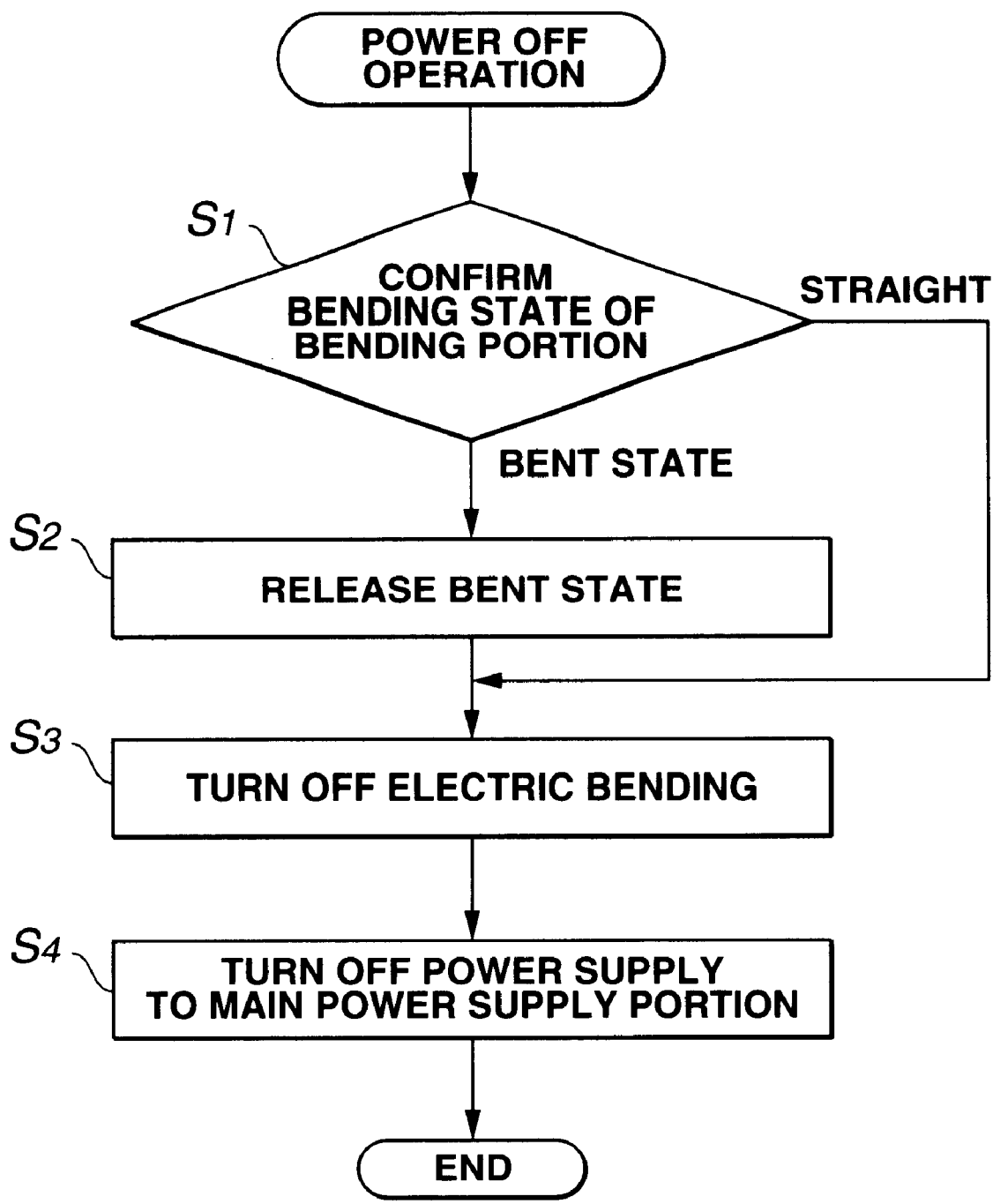
FIG. 3 is a flowchart showing the operation of the system control portion when the power switch is turned OFF during use.

The same operations and results as with the embodiment discussed above are obtained even when the operating sequence as shown in the flowchart in FIG. 3 is combined with the above-mentioned system control portion 43.

In effect, the above-mentioned system control portion 43 continuously detects the state of the power switch 5a established in the above-mentioned remote control device 5. When this system control portion 43 detects that the above-mentioned power switch 5a has been placed in an OFF state by the operator, the bent state of the bending portion 22 is confirmed by the system control portion 43 as shown in Step S1. Here, the process moves to Step 2 when the above-mentioned bending portion 22 is in a bent state, meaning when the bending portion 22 is not straight.

Thereupon, the system control portion 43 outputs a command signal to switch the change-over switch 38 of the motor control portion 35 regardless of the operating command from the joystick 5b of the remote control device 5. The information for fixing the bending angle at 0 degrees is thereby output to the difference computing portion 36 and the bent state of the bending portion 22 is released.

Next, the electric bending is turned OFF as shown in Step S3, then the process moves to Step S4 and the relay switch 51 is turned OFF and the supply of power to the main power supply portion 41 is stopped.

Moreover, when the bending portion 22 is not in the bent state, the process is moved to Step 3 by the above-mentioned system control portion 43. In effect, when it is detected that power is OFF when the bending is not applied and the command signal to switch the change-over switch 38 in the motor control portion 35 is not output, the electric bending is turned OFF without the command for a bending angle of 0 degrees being output and when the process then moves to Step S4, the supply of power to the main power supply portion 41 is stopped.

In this way, when the power switch of the remote control device is put in a power OFF state, the endoscope control device enters an OFF state in a condition where the bent state of the bending portion is automatically released. As a result, withdrawal of the insert portion and the winding up of the insert portion on a drum can be performed in this OFF state. The ease of use of the electric bending endoscope device is thereby greatly improved.

The present invention has varying modes of execution within a broad scope, but clearly these can be constituted on the basis of the present invention without departing from the spirit and scope of the invention. Also, the present invention is not limited by the specific modes of execution, except where limited by the appended claims.

What is claimed is:

1. An electric bending endoscope device comprising:

an endoscope having a bending portion;

a bending control mechanism for electrically driving the bending portion of the endoscope;

a power source voltage monitoring portion for monitoring the source voltage supplied to this bending control mechanism; and a bent state releasing portion for releasing the bent state of the bending portion, when said bending portion is in the bent state, on the basis of an output signal from the source voltage monitoring portion.

2. The electric bending endoscope device according to claim 1, wherein said bent state releasing portion includes a change-over switch for outputting information to release the bent state.

3. An electric bending endoscope device comprising:

an endoscope having a bending portion;

a bending control mechanism for electrically driving and bending the bending portion of the endoscope;

a power source voltage monitoring portion for monitoring the source voltage supplied to this bending control mechanism;

an auxiliary power source for supplying auxiliary power to said bending control mechanism on the basis of an output signal from the source voltage monitoring portion; and a bent state releasing portion for releasing the bent state of the bending portion, when said bending portion is in the bent state, using the power from the auxiliary power source.

4. The electric bending endoscope device, according to claim 3, wherein the auxiliary power is supplied for a set period of time from said auxiliary power source to said bending control mechanism.

5. The electric bending endoscope device, according to claim 3, wherein, when said bending portion is in a bent state and it is detected that the power is in an OFF state during use of said endoscope, said bending control mechanism outputs a signal to release the bent state of said bending portion to said bent state releasing portion.

6. The electric bending endoscope device according to claim 3, wherein said bent state releasing portion includes a change-over switch for outputting information to release the bent state.

* * * * *